United States Patent [19]

Fujimoto

[11] Patent Number: 4,920,139
[45] Date of Patent: Apr. 24, 1990

[54] ALPHA-ALKYL-ALPHA-(4-HALOPHENYL)-1H-1,2,4-TRIAZOLE-1-PROPANENITRILE

[75] Inventor: Ted T. Fujimoto, Churchville, Pa.

[73] Assignee: Rohm and Haas Company, Philadelphia, Pa.

[21] Appl. No.: 211,957

[22] Filed: Jun. 27, 1988

Related U.S. Application Data

[63] Continuation of Ser. No. 551,732, Nov. 10, 1983, abandoned.

[51] Int. Cl.$^5$ .................. A01N 43/653; C07D 249/08
[52] U.S. Cl. ..................................... 514/383; 514/184; 548/101; 548/267.4
[58] Field of Search ................ 548/101, 262; 514/184, 514/383

[56] References Cited

U.S. PATENT DOCUMENTS 4,115,578 6/1978 Miller et al. ..................... 514/399
4,366,165 12/1982 Miller et al. ..................... 514/383

OTHER PUBLICATIONS

Mitsudera, et al., *J. Takeda Res. Lab.*, 41, pp. 148–153 (1982).
Buchel (editor), *Chemistry of Pesticides*, pp. 234 and 238–239, John Wiley & Sons (1983).

*Primary Examiner*—Glennon H. Hollrah
*Assistant Examiner*—Patricia L. Morris
*Attorney, Agent, or Firm*—Polly E. Ramstad

[57] ABSTRACT

This invention relates to alpha-alkyl-alpha-(4-halophenyl)-1H-1,2,4-triazole-1-propanenitriles, their enantiomorphs, acid addition salts and metal salt complexes. These compounds, enantiomorphs, salts and complexes are highly active broad spectrum systemic fungicides effective in controlling phytopathogenicfungi such as barley spot blotch, grape, wheat and bean powdery mildews, grape downy mildew, rice blast, tomato and potato late blights and wheat stem rust.

15 Claims, No Drawings

ALPHA-ALKYL-ALPHA-(4-HALOPHENYL)-1H-1,2,4-TRIAZOLE-1-PROPANENITRILE

This is a continuation of application Ser. No. 551,732, filed Nov. 10, 1983, now abandoned.

BACKGROUND OF THE INVENTION

This invention relates to alpha-alkyl-alpha-(4-halophenyl)-1H-1,2,4-triazole-1-propanenitriles and their use in controlling phytopathogenic fungi.

U.S. Pat. No. 4,366,165 discloses 1 and 4-arylcyanoalkyl-1,2,4-triazoles and their use against phytopathogenic fungi. However, it fails to recognize the particular class of compounds of the present invention which have a particularly high degree of fungicidal activity.

DESCRIPTION OF THE INVENTION

In accordance with the present invention, there is provided a new class of triazole propanenitriles which are 2-alkyl-2-(4-halophenyl)-1H-1,2,4-triazole-1-propanenitriles of the formula (I):

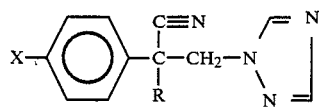

wherein X is a fluoro, chloro or bromo atom; R is $(C_3-C_8)$-alkyl; and the agronomically acceptable enantiomorphs, acid addition salts and metal complexes thereof.

The term "alkyl" is meant to include both branched and straight chained alkyl groups of from 3–8 carbon atoms. Typical alkyl groups which are encompassed by the use of this term are propyl, iso-propyl, n-butyl, sec-butyl, iso-butyl, tert-butyl, pentyl, neo-pentyl, iso-pentyl, hexyl, heptyl, iso-octyl and the like. However, straight chained alkyl groups are preferred and if the alkyl group is branched, it is preferred that the branching does not occur at the alpha carbon of the R substituent.

The acids which can be utilized in making the acid addition salts of the present invention include, for example, hydrochloric, hydrobromic, nitric, sulfuric, phosphoric, hydroiodic, hdyrofluoric, perchloric, p-toluenesulfonic, methanesulfonic, acetic, citric, tartaric, malic, maleic, oxalic, fumaric and phthalic acids.

Another embodiment of this invention is the metal salt complexes of the formula (II):

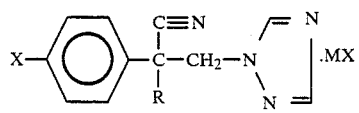

wherein X and R are as defined in formula (I) above and M is a cation selected from Group IIA, IB, IIB, VIB, VIIB and VIII of the Periodic Table and X is an anion selected so that the sum of the valence charges of the cation M and anion X equal zero.

Typical cations encompassed by this invention are magnesium, manganese, copper, nickel, zinc, iron, cobalt, calcium, tin, cadmium, mercury, chromium, lead, barium and the like.

Typical anions encompassed by this invention are chloride, bromide, iodide, fluoride, sulfate, bisulfate, perchlorate, nitrate, nitrate, phosphate, carbonate, bicarbonate, acetate, citrate, oxalate, tartrate, malate, maleate, fumarate, p-toluenesulfonate, methanesulfonate, mono- or di-$(C_1-C_4)$alkyldithiocarbamate, $(C_1-C_4)$alkylenebisdithiocarbamate and the like.

A preferred embodiment of this invention is the compounds, agronomically acceptable enantiomorphs, salts and complexes of formulas (I) and (II) wherein X is fluoro or chloro atom and R is $(C_3-C_6)$alkyl group with the proviso that if it is a branched alkyl, the branching does not occur at the alpha carbon of the R substituent. A more preferred embodiment of this invention is where X is a fluoro or a chloro atom and R is a propyl, n-butyl, iso-butyl or n-pentyl group and a most preferred embodiment is where x is a chloro atom and R is an n- or iso-butyl group.

Typical compounds encompassed by the present invention include:
alpha-(4-chlorophenyl)-alpha-propyl-1H-1,2,4-triazole-1-propanenitrile
alpha-(4-fluorophenyl)-alpha-propyl-1H-1,2,4-triazole-1-propanenitrile
alpha-butyl-alpha-(4-chlorophenyl)-1H-1,2,4-triazole-1-propanenitrile
alpha-butyl-alpha-(4-bromophenyl)-1H-1,2,4-triazole-1-propanenitrile
alpha-butyl-alpha-(4-fluorophenyl)-1H-1,2,4-triazole-1-propanenitrile
alpha-(4-fluorophenyl)-alpha-iso-propyl-1H-1,2,4-triazole-1-propanenitrile
alpha-(4-chlorophenyl)-alpha-iso-butyl-1H-1,2,4-triazole-1-propanenitrile
alpha-(4-bromophenyl)-alpha-sec-butyl-1H-1,2,4-triazole-1-propanenitrile
alpha-(4-chlorophenyl)-alpha-pentyl-1H-1,2,4-triazole-1-propanenitrile
alpha-(4-chlorophenyl)-alpha-isopentyl-1H-1,2,4-triazole-1-propanenitrile
alpha-(4-fluorophenyl)-alpha-hexyl-1H-1,2,4-triazole-1-propanenitrile
alpha-(4-fluorophenyl)-alpha-heptyl-1H-1,2,4-triazole-1-propanenitrile
alpha-(4-chlorophenyl)-alpha-octyl-1H-1,2,4-triazole-1-propanenitrile
and the agronomically acceptable enantiomorphs, acid addition salts and metal salt complexes thereof.

The compounds of the present invention possess curative, residual and preventive antifungal properties against a broad spectrum of phytopathogenic fungi. They additionally may act as systemic and/or contact fungicides. Examples of such fungi include wheat and barley powdery mildew (*Erysiphe graminis*), rice blast (*Piricularia oryzae*), peanut early leaf spot (*Cercospora arachidicola*), banana Sigatoka (*Mycosphaerella fijiensis*), wheat leaf rust (*Puccinia recondita*), wheat stem rust (*Puccinia graminis*), Septoriosis of wheat (*Septoria spp.*), barley net blotch (*Helminthosporium teres*), grape powdery mildew (*Uncinula necator*), grape black rot (*Guignardia bidwellii*), apple scab (*Venturia inequalis*), apple powdery mildew (*Podosphaera lencotricha*), cucumber powdery mildew (*Sphaerotheca fuliginea*), brown rot of stone fruits (*Monilinia fructicola*) and rice sheath blight (*Rhizoctonia solani*).

The triazoles of the present invention can be prepared by conventional synthesis routes. For example, the triazoles may be prepared by nucleophilic displacement of the alkylated phenylacetonitrile bromide (V) by a salt, preferably an alkali metal salt, of the triazole, generally about 1 to about 3 equivalents. This reaction can be run either neat or, preferably, in an appropriate solvent such as dimethylsulfoxide (DMSO), n-dimethylformamide, toluene or xylene at a temperature from about 0° C. to about 150° C., preferably from about 25° to about 100° C. The bromide (V) is prepared by bromomethylation of the alkylated phenylacetonitrile (IV) by methylenebromide (generally about 1.1 to about 2 equivalents) under basic conditions, e.g., sodium or potassium hydroxide, sodium or potassium hydride, potassium methoxide and potassium-t-butoxide (generally about 1.1 to about 2 equivalents) preferably with the use of a solvent such as DMSO, at a temperature from about 0° to about 150° C., preferably from about 25° to about 100° C. The alkylated phenylacetonitriles (IV) can be prepared by phase transfer alkylation of the appropriately substituted benzylcyanides (III) with generally about 1 to about 2 equivalents of an alkyl halide (RX wherein R is as defined above and X is, for example, Cl, Br, I, tosylate or mesylate) in the presence of a strong base, e.g., 50% (w/w) sodium hydroxide or another metal alkoxide, and a catalyst, e.g., tetrabutylammonium bromide. Both the benzylcyanides and the alkyl halides can be readily prepared by techniques known from the literature. This synthesis scheme is shown below:

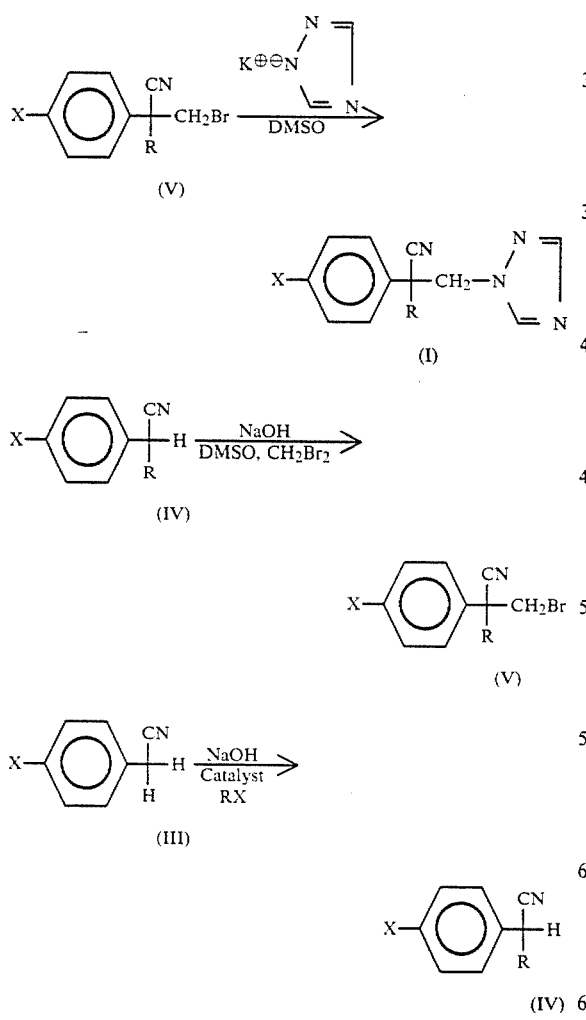

The acid addition salts of the triazoles of this invention can be prepared by standard techniques well-known in the art. For example, the triazole of formula (I) can be dissolved in an appropriate solvent such as diethyl ether, tetrahydrofuran, ethanol, methanol and the like or combinations thereof and treated with an equivalent or excess amount of a mineral or organic acid which may or may not be dissolved in an appropriate solvent, the mixture is then either cooled or evaporated to give the salt which can either be used as such or recrystallized from an appropriate solvent or combination of appropriate solvents.

The metal salt complexes of the above triazoles of this invention can be prepared by adding dropwise, with stirring, a stoichiometric amount of a metal salt dissolved in an appropriate solvent or combination of solvents to a solution of the triazole of formula (I) dissolved in a similarly appropriate solvent or combination of solvents. The reaction mixture is briefly stirred and the solvent is removed under reduced pressure to give the metal salt complex of the respective triazoles of formula (II).

The metal salt complexes can also be prepared by mixing stoichiometric or excess amounts of the metal salt and a triazole of formula (I) in the desired amount of solvent containing the appropriate adjuvants just prior to spraying the plants. Adjuvants that may be included in this "in situ" preparation may be detergents, emulsifiers, wetting agents, spreading agents, dispersing agents, stickers, adhesives, and the like which are used in agricultural applications.

Solvents that can be utilized in these procedures include any polar solvent, e.g., water, methanol, ethanol, isopropanol or ethylene glycol and any aprotic dipolar solvent, e.g., dimethylsulfoxide, acetonitrile, dimethylformamide, nitromethane or acetone.

The metal salt cations that can be used in these procedures can be selected from the group consisting of calcium, magnesium, manganese, copper, nickel, zinc, iron, cobalt, tin, cadmium, mercury, chromium, lead, barium and the like.

Any appropriate anion, e.g., chloride, bromide, iodide, sulfate, bisulfate, phosphate, nitrate, perchlorate, carbonate, bicarbonate, hydrosulfide, hydroxide, acetate, oxalate, malate, citrate and the like may be utilized as the counterion in the metal salt.

The compounds of this invention possess an asymmetric carbon atom and thus exist as racemic mixtures. The d and l enantiomorphs in these racemic mixtures can be separated via standard techniques such as fractional crystallization with d-tartaric acid, l-tartaric acid, l-quinic acid and the like followed by basification and extraction of the d or l enantiomorph free base.

The enantiomorphs, acid addition salts and metal salt complexes of the present invention are useful as agricultural fungicides and as such can be applied to various loci such as the seed, the soil or the foliage. For such purposes these compounds can be used in the technical or pure form as prepared, as solutions or as formulations. The compounds are usually taken up in a carrier or are formulated so as to render them suitable for subsequent dissemination as fungicides. For example, these chemical agents can be formulated as wettable powders, emulsifiable concentrates, dusts, granular formulations, aerosols, or flowable emulsion concentrates. In such formulations, the compounds are extended with a liquid or solid carrier and, when desired, suitable surfactants are incorporated.

It is usually desirable, particularly in the case of foliar spray formulations, to include adjuvants, such as wetting agents, spreading agents, dispersing agents, stickers, adhesives and the like in accordance with agricultural practices. Such adjuvants commonly used in the art can be found in the John W. McCutcheon, Inc. publication "Detergents and Emulsifiers, Annual."

In general, the compounds of this invention can be dissolved in certain solvents such as acetone, methanol, ethanol, dimethylformamide or dimethyl sulfoxide and such solutions can be extended with water. The concentrations of the solution can vary from about 1% to about 90% with a preferred range being from about 5% to about 50%.

For the preparation of emulsifiable concentrates, the compound can be dissolved in suitable organic solvents, or a mixture of solvents, together with an emulsifying agent which permits dispersion of the fungicide in water. The concentration of the active ingredient in emulsifiable concentrates is usually from about 10% to about 90% and in flowable emulsion concentrates, this can be as high as about 75%.

Wettable powders suitable for spraying, can be prepared by admixing the compound with a finely divided solid, such as clays, inorganic silicates and carbonates, and silicas and incorporating wetting agents, sticking agents, and/or dispersing agents in such mixtures. The concentration of active ingredients in such formulations is usually in the range of from about 20% to about 98%, preferably from about 40% to about 75%. A typical wettable powder is made by blending 50 parts of alpha-(4-chlorophenyl)-alpha-butyl-1H-1,2,4-triazole-1-propanenitrile, 45 parts of a syntheic precipitated hydrated silicon dioxide sold under the trademark Hi-Sil ®, and 5 parts of sodium lignosulfonate. In another preparation a kaolin type (Barden) clay is used in place of the Hi-Sil in the above wettable powder, and in another such preparation 25% of the Hi-Sil is replaced with a synthetic sodium silico aluminate sold under the trademark Zeolex ®7.

Dusts are prepared by mixing the triazoles, enantiomorphs, salts and complexes thereof with finely divided inert solids which can be organic or inorganic in nature. Materials useful for this purpose include botanical flours, silicas, silicates, carbonates and clays. One convenient method of preparing a dust is to dilute a wettable powder with a finely divided carrier. Dust concentrates containing from about 20% to about 80% of the active ingredient are commonly made and are subsequently diluted to from about 1% to about 10% use concentration.

The enantiomorphs, salts and complexes thereof can be applied as fungicidal sprays by methods commonly employed, such as conventional high-gallonage hydraulic sprays, low-gallonage sprays, air-blast spray, aerial sprays and dusts. The dilution and rate of application can be readily determined by one in the art depending upon the type of equipment used, the desired method, timing and frequency of applications, plants to be treated and disease to be controlled. Generally, however, the fungicidal compounds of the present invention will be applied in an amount of from about 0.01 to about 20 pounds of active ingredient per acre when applied foliarly or to the soil.

As a seed protectant, the amount of the compound coated on the seeds is usually from about 0.05 to about 4 ounces of active ingredient per hundred pounds of seed and preferably from 0.1 to about 1 ounce per hundred pounds of seed. As a soil fungicide the compounds can be incorporated in the soil or applied to its surface usually at a rate of from about 0.05 to about 20 pounds, preferably from about 0.02 to about 10 pounds and more preferably from about 0.01 to about 3 pounds of active ingredient per acre. As a foliar fungicide, the compounds are usually applied to growing plants at a rate of from about 0.01 to about 10 pounds, preferably from about 0.02 to about 5 and more preferably from about 0.03 to about 1 pound of active ingredient per acre.

Fungicides which can be combined with the fungicides of this invention include:

(a) dithiocarbamate and derivatives such as: ferric dimethyldithiocarbamate (ferbam), zinc dimethyldithiocarbamate (ziram), manganese ethylenebisdithiocarbamate (maneb) and its coordination product with zinc ion (mancozeb), zinc ethylenebisdithiocarbamate (zineb), zinc propylenebisdithiocarbamate (propineb), sodium methyldithiocarbamate (metham), tetramethylthiuram disulfide (thiram), the complex of zineb and polyethylene thiuram disulfide, 3,5-dimethyl-1,3,5-2-H-tetrahydrothiadiazine-2-thione (dazomet); and mixtures of these and mixtures with copper salts;

(b) nitrophenol derivatives such as: dinitro-(1-methylheptyl) phenyl crotonate (dinocap), 2-sec-butyl-4,6-dinitrophenyl 3,3-dimethylacrylate (binapacryl), and 2-sec-butyl-4,6-dinitrophenyl isopropyl carbonate;

(c) heterocyclic structures such as: N-trichloromethylthiotetrahydrophthalimide (captan), N-trichloromethylthiophthalimide (folpet), 2-heptadecyl-2-imidazole acetate (glyodine), 2-octylisothiazol-3-one, 2,4-dichloro-6-(o-chloroanilino)-s-triazine, diethyl phthalimidophosphorothioate, 4-butyl-1,2,4-triazole, 5-amino-1[bis(dimethylamino)-phosphinyl]-3-phenyl-1,2,4-triazole, 5-ethoxy-3-trichloromethyl-1,2,4-thiadiazole, 2,3-dicyano-1,4-dithiaanthraquinone (dithianon), 2-thio-1,3-dithio-[4,5-b]quinoxaline (thioquinox) methyl 1-(butylcarbamoyl)-2-benzimidazole carbamate-(benomyl),2-(4'-thiazolyl)benzimidazole-(thiabendazole), 4-(2-chlorophenylhydrazono)-3-methyl-5-isoxazolone, pyridine-2-thiol-1-oxide, 8-hydroxyquinoline sulfate and metal salts thereof; 2,3-dihydro-5-carboxanilido-6-methyl-1,4-oxathiin-4,4-dioxide, 2,3-dihydro-5-carboxanilido-6-methyl-1,4-oxathiin,alpha-(phenyl)-alpha-(2,4-dichlorophenyl)-5-pyrimidinyl-melthanol (triarimol), cis-N-[(1,1,2,2-tetrachloroethyl)thio]-4-cyclohexene-1,2-dicarboxyimide, 3-[2-(3,5-dimethyl-2-oxycyclohexyl)-2-hydroxy]-glutarimide (cyclohexiimide), dehydroacetic acid, N-(1,1,2,2-tetrachloroethylthio)-3a,4,7,7a-tetrahydrophthalimide (captafol), 5-butyl-2-ethylamino-4-hydroxy-6-methylpyrimidine (ethirimol), acetate of 4-cyclododecyl-2,6-dimethylmorpholine (dodemorph), and 6-methyl-2-oxo-1,3-dithiolo-[4,5-b]quinoxaline (quinomethionate).

(d) miscellaneous halogenated fungicides such as: tetrachloro-p-benzoquinone (chloranil), 2,3-dichloro-1,4-naphthoquinone (dichlone), 1,4-dichloro-2,5-dimethoxybenzene (chloroneb), 3,5,6-trichloro-o-anisic acid (tricamba), 2,4,5,6-tetrachloroisophthalonitrile (TCPN), 2,6-dichloro-4-nitroaniline (dichloran), 2-chloro-1-nitropropane, polychloronitrobenzenes such as: pentachloronitrobenzene (PCNB) and tetrafluorodichloroacetone;

(e) fungicidal antibiotics such as: griseofulvin, kasugamycin and streptomycin;

(f) copper-based fungicides such as: cuprous oxide, basic cupric chloride, basic copper carbonate, copper naphthenate, and Bordeaux mixture; and (g) miscellaneous fungicides such as: diphenyl, dodecylguanidine acetate (dodine), phenylmercuric acetatic, N-ethylmercuri-1,2,3,6-tetrahydro-3,6-endomethano-3,4,5,6,7,7-hexachlorophthalimide, phenylmercuric monoethanol ammonium lactate, p-dimethylaminobenzenediazo sodium sulfonate, methyl isothiocyanate, 1-thiocyano-2,4-dinitrobenzene, 1-phenylthiosemicarbazide, nickel-containing compounds, calcium cyanamide, lime sulfur, sulfur, and 1,2-bis(3-methoxycarbonyl)-2-thioureido)benzene(thiophanatemethyl).

The enantiomorphs, acid addition salts and metal salt complexes of this invention can be advantageously employed in various ways. Since these compounds possess broad spectrum fungicidal activity, they can be employed as fungicides in turf, fruit orchards, vegetable crops, cereal crops, golf course applications and the storage of cereal grain. Other applications of this invention will suggest themselves to those skilled in the art of agriculture and horticulture.

EXAMPLES

EXAMPLE 1: Preparation of alpha-butyl-alpha-(4-chlorophenyl)-1H-1,2,4-triazole-1-propanentrile (A) 1-bromo-2-cyano-2-(4-chlorophenyl)hexane In a 300 ml three neck flask fitted with a mechanical stirrer, thermometer and addition funnel was added 20.8 gm (0.1 mol) of (p-chlorophenyl)hexanenitrile, 34.8 gm (0.2 mol) of methylene bromide and 50 ml of DMSO. To the reaction flask was added 24 ml of 50% (w/w) sodium hydroxide, dropwise over a 35 minute period. Upon completion of the reaction, it was quenched by adding 500 ml of water. The aqueous mixture was extracted three times with ether, then the combined ether extracts were washed three times with water and once with brine. The organic phase was dried over sodium sulfate, filtered and the solvent removed by rotary evaporation yielding 22.6 gm of a yellow oil.

NMR: 60 mHz 0.8–2.0 δ (m, 9H), 4.0 δ (br, s, 2H) and 7.4 δ (s, 2H).

(B) Alpha-butyl-alpha-(4-chlorophenyl)-1H-1,2,4-triazole-1-propanenitrile

In a single neck 500 ml flask fitted with a magnetic stirrer and drying tube was added 26.6 gm (0.09 mol) of 1-bromo-2-cyano-2-(4-chlorophenyl)hexane, followed by 19.0 gm of potassium triazole (0.18 mol) and 100 ml of DMSO. The reaction was stirred for about 48 hours at room temperature and then stirred for about 24 hours at 70° C. The reaction was quenched by pouring it into 1500 ml of water. The aqueous mixture was extracted four times with ether and the combined either extracts were washed twice with water and once with brine. The organic phase was dried over sodium sulfate, concentrated and redissolved in a minimum amount of ether. Hexane was added until the solution was cloudy, and then flask was placed in the freezer. The crystals which formed were filtered off and dried. The filtrate was concentrated to obtain additional less pure material for a total of 13.0 gm.

Elemental Analysis—Theoretical (Found): C: 62.36(62.55, 62.38); H: 5.94(6.07, 6.00); N: 19.41(19.22, 19.35); Cl: 12.28(11.00, 11.90).

EXAMPLE 2: Preparation of alpha-(4-chlorophenyl)-alpha-propyl-1H-1,2,4-triazole-1-propanenitrile (A) 2-(4-chlorophenyl)pentanenitrile In a four neck one liter flask fitted with a reflux condenser, mechanical stirrer and addition funnel was placed 227.4 gm (1.5 mol) of 4-chlorophenylacetonitrile, 235.6 gm (3.0 mol) of 1-chloropropane and 4.8 gm (0.15 mol) of tetrabutylammonium bromide. 300 gm (3.75 mol) of 50% (w/w) NaOH was added dropwise over 30 minutes. The reaction mixture quickly exothermed to 50° C. and the reaction flask was placed in a cold water bath until the reaction mixture cooled to 35° C. Thereafter, the reaction mixture was heated for an additional 4 hours at 50° C., then the reaction was quenched by adding 1500 ml of water. The mixture was extracted twice with ether and the organic phase was washed with water and then with 200 ml of 10% (w/w) hydrochloric acid. The ether was dried, filtered, concentrated and distilled. The distillate was collected, at 105° C. at 0.5 mm, and two main fractions of 156.3 gm (88% purity) and 88 gm (60% purity) were obtained. The higher purity material was used in the bromomethylation of step B.

NMR: 60 mHz (d-CHCl₃): 1.0–2.0 δ (m, 7H), 3.8–3.9 δ (t, 1H) and 7.5 δ (s, 4H).

(B) 1-bromo-2-cyano-2-(4-chlorophenyl)pentane

In a 2000 ml four neck flask fitted with a reflux condenser, mechanical stirrer, thermometer and addition funnel was placed 305.0 mg (1.57 mol) of 2-(4-chlorophenyl)pentanenitrile, 409.4 gm (2.36 mol) of dibromomethane and 400 ml of DMSO. 50% (w/w) sodium hydroxide (251.2 gm, 3.00 mol) was added dropwise over 2 hours with the reaction temperature rising to 50° C. A water bath was used to maintain the reaction at about 40° C. and after about 4 hours, the reaction was quenched by adding 100 ml of water. After sitting at room temperature for about 16 hours, the mixture was diluted with 1000 ml of ice water, extracted with ether, the combined ether extracts were washed twice with water and then with 10% (w/w) hydrochloric acid and dried over sodium sulfate. The ether was removed by rotary evaporation and the remaining DMSO removed under high vacuum to yield 361.2 gm of the bromide derivative.

NMR: 60 mHz (d-CHCl₃) 1.0–2.2 δ (m, 7H), 4.0 δ (br s, 2H) and 7.5 δ (s, 4H).

(C) alpha-propyl-alpha-(4-chlorophenyl)-1H-1,2,4-triazoles-1-propanenitrile

In a single neck one liter flask was placed 361.2 gm (1.26 mol) of 1-bromo-2-cyano-2-(4-chlorophenyl)pentane and 300 ml of DMSO. The potassium salt of triazole (270.0 gm, 2.52 mol) was added and the flask was placed on a rotary evaporator for 1 hour at 75° C. to dissolve the triazole salt. The flask was then heated at 90° C. for 4 hours, followed by stirring at room temperature overnight (about 16 hours). The reaction was found to be incomplete and reheated to 120° C. for about 12 hours followed by stirring it at 90° C. for about 36 hours. Upon completion of the reaction, the reaction mixture was cooled to room temperature and diluted with 1500 ml of ice water. The water was extracted with 250 ml of ether; however, since the product crystallized in the ether layer, this layer was then diluted with 1500 ml of ethyl acetate and extracted. The water layer was additionally extracted twice with ethyl acetate and the combined organic extracts were separated into two batches. Each was extracted with water (6×150 ml) and once with brine. The dark brown organic phase was dried over sodium sulfate and then filtered. The solution was treated then with activated charcoal and filtered and stripped to give a crystalline cake which was recrystallized from ethyl acetate:ether. The product was kept in the freezer for 16 hours and then filtered and washed with hexane. The filtrate was concentrated, hexane added and then triturated to yield an additional solid which was combined with the first crop to give 166.8 gm of product.

M.P.: 108°–110° C.

Elemental Analysis—Theoretical (Found): C: 61.20(61.16); H: 5.50(5.56); N: 20.39(20.26); Cl: 12.91(12.66).

EXAMPLE 3: Preparation of alpha-butyl-alpha-(4-fluorophenyl)-1H-1,2,4-triazole-1-propanenitrile (A) 2-(4-fluorophenyl)hexanitrile The phase transfer procedure was employed as with 2-(4-chlorophenyl)pentanenitrile, with 400 gm (2.96 mol) of p-fluorophenylacetonitrile, 548 gm (5.92 mol) of 1-chlorobutane, 592 gm (7.4 mol) of 50% (w/w) sodium hydroxide and 9.07 gm (0.3 mol) of tetrabutylammonium bromide. The base was added over 2.5 hours with the reaction temperature rising to 35° C. The reaction was then stirred for about 12 hours at 45° C. Upon completion, the reaction was quenched with water and the mixture was extracted and washed as in Example 1 and then distilled to yield 358.8 gm of 91% pure product.

NMR data: 60 mHz (d-CHCl$_3$): 0.8–2.0 δ (m, 9H), 3.7–3.8 δ (t, 1H) and 7.4–7.5 δ (br s, 4H).

(B) 1-bromo-2-cyano-2-(4-fluorophenyl)hexane

The bromomethylation procedure of Example 1 was employed using 358.1 gm (1.875 mol) of 50% (w/w) sodium hydroxide, 488.9 gm (2.81 mol) of dibromomethane and 400 ml of DMSO. Sodium hydroxide (50%, w/w) was added dropwise over about 2 hours with the reaction exotherming to 90° C. The reaction mixture was cooled to 50° C. and the mixture was stirred for 11 hours until the reaction was about 90% complete. The reaction was quenched and worked up in the manner described in Example 1A to yield 379.5 gm of a 88% pure product. The product was used directly to prepare the triazole adduct.

NMR: 0.8–2.0 δ (m, 9H), 4.0 δ (br s, 2H), and 7.4 δ (s, 4H).

(C) Alpha-butyl-alpha-(4-fluorophenyl)-1H-1,2,4-triazole-1-propanenitrile

In a 2 liter four neck flask was placed 379.5 gm (1.33 mol) of 1-bromo-2-cyano-2-(4-fluorophenyl)-hexane and 300 ml of DMSO to which 156 gm (1.46 mol) of potassium triazole was added. The reaction mixture was stirred overnight at 90° C. The product was worked up in the manner described in Example 1B to yield 340.5 gm of a semisolid, 83% pure.

NMR data: 60 mHz (d-CHCl$_3$): 1.0–2.2 δ (m, 9H), 4.8 δ (s, 2H), 7.0–7.8 δ (m, 4H), 8.05 δ (s, 1H) and 8.10 δ (s, 1H).

EXAMPLE 4: Preparation of alpha-(4-fluorophenyl)-alpha-propyl-1H-1,2,4-triazole-1-propanenitrile (A) 2-(4-fluorophenyl)pentanenitrile)

To 50.0 gm (0.37 mol) of 4-fluorophenylacetonitrile, 0.6 gm of tetraethyl ammonium bromide, 50 gm (0.407 mol) of 1-bromopropane and 50 ml of DMSO was added 35.5 gm (0.44 mol) of 50% (w/w) sodium hydroxide at room temperature. After the addition was complete, the reaction was stirred at 50°–60° C. for 3 hours. The reaction mixture was extracted with ether, the organic phase washed with water and then 10% (w/w) hydrochloric acid. The ether was dried, filtered and distilled to give 23 grams of the product (b.p. 105°–110° C. at 5 mm).

NMR: 60 mHz (d-CHCl$_3$) 0.9–2.2 δ (m, 7H), 3.8–4.0 δ (t, 1H), 7.0–7.6 δ (m, 4H).

(B) 1-bromo-2-cyano-2-(4-fluorophenyl)pentane

The bromomethylation of the previous examples was employed using 23.0 gm (0.129 mol) of 2-(4-fluorophenyl)pentanenitrile and 22.5 gm (0.129 mol) of dibromoethane in 50 ml of DMSO. To the reaction mixture was added 11.95 gm (0.15 mol) of 50% (w/w) sodium hydroxide while stirring at room temperature. The reaction was heated to 60° C. for 3 hours, cooled to room temperature and worked up in the manner described in the previous examples, e.g., 3B. There was obtained 20.5 gm of the bromide derivative which was used directly below in step C.

b.p. 105°–110° C. at 5 mm

NMR: 0.7–2.2 δ (m, 7H), 3.9 δ (q, 2H), and 7.0–7.8 δ (m, 4H).

(C) Alpha-(4-fluorophenyl)-alpha-propyl-1H-1,2,4-triazole-1-propanenitrile

To a solution of 8.1 gm (0.76 mol) of potassium triazole and 30 ml of DMSO was added with 15 gm (0.58 mol) of 1-bromo-2-cyano-2-(4-fluorophenyl)pentane while maintaining the temperature at 50° C. While stirring, the reaction mixture was heated further to 80° C. for 1 hour and then heated at 100° C. for 24 hours. The product was worked up as described in Example 3C and after concentration and trituration, 1.3 gm of a white solid, m.p. 75°–76° C., was obtained.

Elemental Analysis—Theoretical (Found): C: 65.09(64.80); H: 5.86(5.95); N: 21.69(20.77); F: 7.36(7.02).

NMR: 90 mHz (d-CHCl$_3$) 0.9–1.0 δ (t, 3H), 1.2–1.8 δ (m, 2H), 1.9–2.2 δ (t, 2H), 3.7–3.9 δ (q, 2H), 7.0–7.5 δ (m, 4H) and 7.9 δ (br s, 2H).

EXAMPLE 5:

The compounds of Examples 1–4 were tested for their antifungal activity against wheat leaf rust (WLR), wheat powdery mildew (WPM) and barley spot blotch (BSB). The test procedures were as follows:

(A) Wheat Leaf Rust (*Puccinia recondita*):

Pennoll wheat seedlings about 7 days old were sprayed to runoff with a solution of the test compound comprising 75 parts per million of the test compound suspended in a 2:1:1 mixture of water, acetone and methanol. After drying, the plants were inoculated with a uredial suspension of *P. recondita* (20,000 uredial/ml). The plants were incubated at 22° C. in a mist for 24 hours. After seven days of futher incubation on a greenhouse bench, the percent disease control was determined by counting uredial pustules and comparing it to the number of pustules on control plants.

B) Wheat Powdery Mildew (*Erysiphe Graminis* f. sp. *tritici*):

Pennoll wheat seedlings (7-14 days old) were trimmed to provide a uniform plant height and to facilitate unifrom inoculation. Twenty-four hours after their trimming, they were sprayed to runoff with a test compound comprising 5 parts per million of the test compound suspended in a 2:1:1 mixture of water, acetone and methanol. Then mildew spores of wheat powdery mildew cultured on wheat seedlings in a controlled temperature room were shaken from the cultured plants onto the Pennoll wheat seedlings. The inoculated seedlings were kept in the controlled temperature room and subirrigated. The percent disease control was rated 8-10 days after inoculation.

(C) Barley Spot Blotch (*Helminthosporium sativum*):

Pennrad barley seedlings about 7 days old were sprayed to runoff with a test compound comprising 10 parts per million of the test compound suspended in a 2:1:1 mixture of water, acetone and methanol. After drying, the plants were inoculated with a conidial suspension of *H. sativum* (20,000 conidia/ml). The plants were incubated at 22° C. in a mist for 24 hours. After five days of further incubation on a greenhouse bench, the percent disease control was measured by counting lesions and comparing it to the number of lesions on the control plants.

The results of the tests are presented below in Table 1. The disease control ratings utilized in Table 1 are as follows: A=97–100% disease control, B=90–96% disease control, C=70–89% disease control, D=50–69% disease control and E=49% or less disease control.

TABLE 1

| Compound | Disease Control Rating | | |
|---|---|---|---|
| | WLR | WPM | BSB |
| 1 | A | A | B |
| 2 | A | A | A |
| 3 | A | B | B |
| 4 | A | A | C |

What is claimed is:

1. A compound of the formula

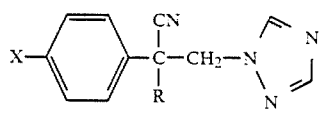

wherein X is a fluoro, chloro or bromo atom, R is $(C_3-C_8)$alkyl group wherein when R is branched, the branching does not occur at the alpha carbon of the R substituent and the agronomically acceptable enantiomorphs, acid addition and metal salt complexes thereof.

2. The compound of claim 1 wherein X is a fluoro or chloro atom and R is $(C_3-C_6)$alkyl group.

3. The compound of claim 1 wherein R is n-propyl, n-butyl, iso-butyl or n-pentyl.

4. The compound of claim 3 wherein X is a fluoro or chloro atom and R is an n-propyl or n-butyl.

5. A compound selected from the group consisting of alpha-butyl-alpha-(4-chlorophenyl)-1H-1,2,4-triazole-1-propanenitrile, alpha-butyl-alpha-(4-fluorophenyl)-1H-1,2,4-triazole-1-propanenitrile, alpha-(4-chlorophenyl)-alpha-n-propyl-1H-1,2,4-triazole-1-propanenitrile and alpha-(4-fluorophenyl)-alpha-n-propyl-1H-1,2,4-triazole-1-propanenitrile and agronomically acceptable enantiomorphs, acid addition salts and metal salt complexes thereof.

6. A compound selected from the group consisting of alpha-n-butyl-(4-chlorophenyl)-1H-1,2,4-triazole-1-propanenitrile and alpha-n-butyl-(4-fluorophenyl)-1H-1,2,4-triazole-1-propanenitrile.

7. The compound of claim 6 which is alpha-n-butyl-alpha-(4-chlorophenyl)-1H-1,2,4-triazole-1-propanenitrile and its agronomically acceptable acid addition salts.

8. A fungicidal composition for controlling phytopathogenic fungi which comprises a fungicidally effective amount of the compound of claim 1 and an agronomically acceptable carrier.

9. A fungicidal composition for controlling phytopathogenic fungi which comprises an agronomically acceptable carrier and as the active ingredient, a fungicidally effective amount of the compound of claim 6.

10. A fungicidal composition for controlling phytopathogenic fungi which comprises a fungically effective amount of the compound of claim 7 and an agronomically acceptable carrier.

11. A fungicidal composition for controlling phytopathogenic fungi which comprises an agronomically acceptable carrier and as the active ingredient, a fungicidally-effective amount of the compound of claim 2 or 3.

12. A method for controlling phytopathogenic fungi comprising applying to a plant, to plant seed or to a plant habitat a fungicidally effective amount of the compound of claim 1.

13. A method for controlling phytopathogenic fungi comprising applying to a plant, to plant seed or to a plant habitat a fungicidally effective amount of the compound of claim 6.

14. A method for controlling phytopathogenic fungi comprising applying to a plant, to plant seed or to a plant habitat a fungicidally effective amount of the compound of claim 7.

15. A method for controlling phytopathogenic fungi comprising applying to a plant, to plant seed or to a plant habitat a fungicidally effective amount of the compound of claim 2 or 3.

* * * * *